US010349976B2

(12) United States Patent
Kick et al.

(10) Patent No.: US 10,349,976 B2
(45) Date of Patent: Jul. 16, 2019

(54) EXPANDABLE PERCUTANEOUS SHEATH

(71) Applicant: Onset Medical, Inc., Irvine, CA (US)

(72) Inventors: George F. Kick, Casa Grande, AZ (US); Thanh Van Nguyen, Irvine, CA (US); Samuel M. Shaolian, Newport Beach, CA (US)

(73) Assignee: Onset Medical, Inc., Irvine, CA (US)

( * ) Notice: Subject to any disclaimer, the term of this patent is extended or adjusted under 35 U.S.C. 154(b) by 0 days.

(21) Appl. No.: 15/006,025

(22) Filed: Jan. 25, 2016

(65) Prior Publication Data

US 2016/0135840 A1    May 19, 2016

Related U.S. Application Data

(63) Continuation of application No. 10/728,728, filed on Dec. 5, 2003, now Pat. No. 9,241,735.

(51) Int. Cl.
| | |
|---|---|
| *A61B 17/34* | (2006.01) |
| *A61M 25/06* | (2006.01) |
| *A61M 31/00* | (2006.01) |
| *A61M 25/00* | (2006.01) |
| *A61B 17/02* | (2006.01) |

(52) U.S. Cl.
CPC ...... *A61B 17/3423* (2013.01); *A61B 17/3415* (2013.01); *A61B 17/3417* (2013.01); *A61B 17/3421* (2013.01); *A61B 17/3439* (2013.01); *A61M 25/0662* (2013.01); *A61M 25/0668* (2013.01); *A61M 31/005* (2013.01); *A61B 2017/0225* (2013.01); *A61B 2017/3486* (2013.01); *A61M 2025/0024* (2013.01); *A61M 2025/0681* (2013.01)

(58) Field of Classification Search
CPC ............ A61B 17/3415; A61B 17/3417; A61B 17/3421; A61B 17/3423; A61B 17/3439
See application file for complete search history.

(56) References Cited

U.S. PATENT DOCUMENTS

| | | |
|---|---|---|
| 319,296 A | 6/1885 | Molesworth |
| 668,879 A | 2/1901 | Miller |
| (Continued) | | |

FOREIGN PATENT DOCUMENTS

| | | |
|---|---|---|
| EP | 0177177 | 4/1986 |
| EP | 0249456 | 12/1987 |
| (Continued) | | |

OTHER PUBLICATIONS

United States Patent and Trademark Office, Notice of Allowance dated Sep. 16, 2015 in U.S. Appl. No. 10/728,728, 9 pages.

(Continued)

*Primary Examiner* — Kathleen S Holwerda
*Assistant Examiner* — Sarah A Simpson
(74) *Attorney, Agent, or Firm* — Inskeep IP Group, Inc.

(57) ABSTRACT

Disclosed is an expandable percutaneous sheath, for introduction into the body while in a first, low cross-sectional area configuration, and subsequent expansion to a second, enlarged cross-sectional configuration. The sheath is maintained in the first, low cross-sectional configuration by a tubular restraint. In one application, the sheath is utilized to provide access for a diagnostic or therapeutic procedure such as percutaneous nephrostomy or urinary bladder access.

19 Claims, 10 Drawing Sheets

(56) References Cited

U.S. PATENT DOCUMENTS

| | | | |
|---|---|---|---|
| 1,213,001 A | 1/1917 | Philips | |
| 1,248,492 A | 12/1917 | Hill | |
| 2,042,900 A | 6/1936 | James | |
| 2,548,602 A | 4/1951 | Greenburg | |
| 3,509,883 A | 5/1970 | Dibelius | |
| 3,545,443 A | 12/1970 | Ansari | |
| 3,742,958 A | 7/1973 | Rundles | |
| 3,789,852 A | 2/1974 | Kim et al. | |
| 3,902,492 A | 9/1975 | Greenhalgh | |
| 4,018,230 A | 4/1977 | Ochiai et al. | |
| 4,141,364 A | 2/1979 | Schultze | |
| 4,338,942 A | 7/1982 | Fogarty | |
| 4,401,433 A | 8/1983 | Luther | |
| 4,411,655 A | 10/1983 | Schreck | |
| 4,451,256 A | 5/1984 | Weikl et al. | |
| 4,479,497 A | 10/1984 | Fogarty et al. | |
| 4,581,025 A | 4/1986 | Timmermans | |
| 4,589,868 A | 5/1986 | Dretler | |
| 4,601,713 A | 7/1986 | Fuqua | |
| 4,610,668 A | 9/1986 | Silvestrini et al. | |
| 4,636,346 A | 1/1987 | Gold et al. | |
| 4,637,396 A * | 1/1987 | Cook | A61M 25/10 604/103 |
| 4,650,466 A | 3/1987 | Luther | |
| 4,710,181 A | 12/1987 | Fuqua | |
| 4,716,901 A | 1/1988 | Jackson et al. | |
| 4,738,666 A * | 4/1988 | Fuqua | A61M 25/0023 604/103.05 |
| 4,739,762 A | 4/1988 | Palmaz | |
| 4,748,666 A | 5/1988 | Fuqua | |
| 4,772,266 A | 9/1988 | Groshong | |
| 4,790,817 A | 12/1988 | Luther | |
| 4,798,193 A | 1/1989 | Giesy et al. | |
| 4,846,791 A | 7/1989 | Hattler et al. | |
| 4,865,593 A | 9/1989 | Ogawa et al. | |
| 4,869,717 A | 9/1989 | Adair | |
| 4,884,573 A | 12/1989 | Wijay et al. | |
| 4,888,000 A | 12/1989 | McQuilkin et al. | |
| 4,896,669 A | 1/1990 | Bhate et al. | |
| 4,898,581 A | 2/1990 | Jang et al. | |
| 4,899,729 A | 2/1990 | Gill et al. | |
| 4,921,479 A | 5/1990 | Grayzel | |
| 4,954,126 A | 9/1990 | Wallsten | |
| 4,955,895 A | 9/1990 | Sugiyama et al. | |
| 4,972,827 A | 11/1990 | Kishi et al. | |
| 4,984,564 A | 1/1991 | Yuen | |
| 4,986,830 A | 1/1991 | Owens et al. | |
| 5,001,488 A | 4/1991 | Ginsburg et al. | |
| 5,011,488 A | 4/1991 | Ginsburg et al. | |
| 5,035,686 A | 7/1991 | Crittenden et al. | |
| 5,045,056 A | 9/1991 | Behl | |
| 5,057,092 A | 10/1991 | Webster, Jr. | |
| 5,066,285 A | 11/1991 | Lundquist et al. | |
| 5,073,166 A | 12/1991 | Parks et al. | |
| 5,078,736 A | 1/1992 | Behl | |
| 5,092,839 A | 3/1992 | Kipperman | |
| 5,098,393 A | 3/1992 | Amplatz et al. | |
| 5,100,388 A | 3/1992 | Behl et al. | |
| 5,108,413 A | 4/1992 | Moyers | |
| 5,108,416 A | 4/1992 | Ryan et al. | |
| 5,112,304 A | 5/1992 | Barlow et al. | |
| 5,112,308 A | 5/1992 | Olsen et al. | |
| 5,116,318 A | 5/1992 | Hillstead | |
| 5,122,122 A | 6/1992 | Allgood | |
| 5,139,511 A | 8/1992 | Gill et al. | |
| 5,147,316 A | 9/1992 | Castillenti | |
| 5,158,545 A * | 10/1992 | Trudell | A61F 2/90 604/104 |
| 5,163,903 A | 11/1992 | Crittenden et al. | |
| 5,176,659 A | 1/1993 | Mancini | |
| 5,183,464 A * | 2/1993 | Dubrul | A61M 25/0662 604/104 |
| 5,188,602 A | 2/1993 | Nichols | |
| 5,201,756 A | 4/1993 | Horzewski et al. | |
| 5,222,938 A | 6/1993 | Behl | |
| 5,222,971 A | 6/1993 | Willard et al. | |
| 5,234,425 A | 8/1993 | Fogarty et al. | |
| 5,250,025 A | 10/1993 | Sosnowski et al. | |
| 5,250,033 A | 10/1993 | Evans et al. | |
| 5,256,150 A | 10/1993 | Quiachone et al. | |
| 5,275,611 A | 1/1994 | Behl | |
| 5,295,994 A | 3/1994 | Bonutti | |
| 5,312,360 A | 5/1994 | Behl | |
| 5,312,417 A | 5/1994 | Wilk | |
| 5,316,360 A | 5/1994 | Feikma | |
| 5,318,588 A | 6/1994 | Horzewski et al. | |
| 5,320,611 A | 6/1994 | Bonutti et al. | |
| 5,324,261 A | 6/1994 | Amundson et al. | |
| 5,346,503 A | 9/1994 | Chow et al. | |
| 5,380,304 A | 1/1995 | Parker | |
| 5,392,677 A | 2/1995 | Masterson et al. | |
| 5,395,341 A | 3/1995 | Slater | |
| 5,395,349 A | 3/1995 | Quiachon et al. | |
| 5,407,430 A | 4/1995 | Peters | |
| 5,409,469 A | 4/1995 | Schaerf | |
| 5,431,676 A | 7/1995 | Dubrul et al. | |
| 5,433,708 A | 7/1995 | Nichols et al. | |
| 5,447,503 A | 9/1995 | Miller | |
| 5,454,790 A | 10/1995 | Dubrul | |
| 5,460,170 A | 10/1995 | Hammerslag | |
| 5,507,767 A | 4/1996 | Maeda et al. | |
| 5,514,091 A | 5/1996 | Yoon | |
| 5,514,236 A | 5/1996 | Avellanet et al. | |
| 5,527,336 A | 6/1996 | Rosenbluth | |
| 5,540,658 A | 7/1996 | Evans et al. | |
| 5,542,928 A | 8/1996 | Evans et al. | |
| 5,549,635 A | 8/1996 | Solar | |
| 5,571,089 A | 11/1996 | Crocker | |
| 5,573,509 A | 11/1996 | Thornton | |
| 5,573,517 A | 11/1996 | Bonutti et al. | |
| 5,573,520 A | 11/1996 | Schwartz | |
| 5,657,963 A | 8/1997 | Hincliffe et al. | |
| 5,662,614 A | 9/1997 | Edoga | |
| 5,674,240 A | 10/1997 | Bonutti et al. | |
| 5,674,857 A | 10/1997 | Anderson et al. | |
| 5,700,253 A | 12/1997 | Parker | |
| 5,702,373 A | 12/1997 | Samson | |
| 5,709,713 A | 1/1998 | Evans et al. | |
| 5,713,867 A | 2/1998 | Morris | |
| 5,738,667 A | 4/1998 | Solar | |
| 5,766,203 A | 6/1998 | Imran et al. | |
| 5,776,141 A | 7/1998 | Klein et al. | |
| 5,810,776 A | 9/1998 | Bacich et al. | |
| 5,817,100 A | 10/1998 | Igaki | |
| 5,846,251 A | 12/1998 | Hart | |
| 5,868,779 A | 2/1999 | Ruiz | |
| 5,869,719 A | 2/1999 | Tsukernik | |
| 5,885,217 A | 3/1999 | Gisselberg et al. | |
| 5,888,196 A | 3/1999 | Bonutti | |
| 5,897,557 A | 4/1999 | Chin et al. | |
| 5,902,282 A | 5/1999 | Balbierz | |
| 5,908,435 A | 6/1999 | Samuels | |
| 5,916,145 A | 7/1999 | Chu et al. | |
| 5,922,019 A | 7/1999 | Hankh et al. | |
| 5,961,499 A | 10/1999 | Bonutti et al. | |
| 5,964,730 A | 10/1999 | Williams et al. | |
| 5,971,938 A | 10/1999 | Hart et al. | |
| 5,997,508 A | 12/1999 | Lunn et al. | |
| 6,030,364 A | 2/2000 | Durgin et al. | |
| 6,056,718 A | 5/2000 | Funderburk et al. | |
| 6,063,056 A | 5/2000 | Engelberg | |
| 6,080,174 A | 6/2000 | Dubrul et al. | |
| 6,090,072 A | 7/2000 | Kratoska et al. | |
| 6,120,480 A | 9/2000 | Zhang et al. | |
| 6,123,689 A | 9/2000 | To et al. | |
| 6,168,579 B1 | 1/2001 | Tsugita | |
| 6,183,443 B1 | 2/2001 | Kratoska et al. | |
| 6,187,000 B1 | 2/2001 | Davison et al. | |
| 6,197,016 B1 | 3/2001 | Fourkas et al. | |
| 6,228,052 B1 | 5/2001 | Pohndorf | |
| 6,248,116 B1 | 6/2001 | Chevillon et al. | |
| 6,280,452 B1 | 8/2001 | Mears | |
| 6,293,909 B1 | 9/2001 | Chu et al. | |
| 6,312,443 B1 | 11/2001 | Stone | |

(56) References Cited

U.S. PATENT DOCUMENTS

| | | | |
|---|---|---|---|
| 6,358,238 B1 | 3/2002 | Sherry | |
| 6,443,979 B1 | 9/2002 | Stalker et al. | |
| 6,447,540 B1 | 9/2002 | Fontaine et al. | |
| 6,471,684 B2 | 10/2002 | Dulak et al. | |
| 6,494,860 B2 | 12/2002 | Rocamora et al. | |
| 6,494,893 B2 | 12/2002 | Dubrul et al. | |
| 6,517,551 B1 | 2/2003 | Driskill | |
| 6,524,268 B2 | 2/2003 | Hayner et al. | |
| 6,524,320 B2 | 2/2003 | DiPoto | |
| 6,530,902 B1 | 3/2003 | Jonkman | |
| 6,582,395 B1 | 6/2003 | Burkett et al. | |
| 6,613,038 B2 | 9/2003 | Bonnutti et al. | |
| 6,613,062 B1 | 9/2003 | Leckrone et al. | |
| 6,616,678 B2 | 9/2003 | Nishtala et al. | |
| 6,638,268 B2 | 10/2003 | Niazi | |
| 6,679,902 B1 | 1/2004 | Boyle et al. | |
| 6,692,462 B2 | 2/2004 | Mackenzie et al. | |
| 6,706,017 B1 | 3/2004 | Dulguerov | |
| 6,808,520 B1* | 10/2004 | Fourkas | A61B 17/3462 604/164.09 |
| 6,827,683 B2 | 12/2004 | Otawara | |
| 6,951,555 B1 | 10/2005 | Suresh et al. | |
| 7,033,369 B2 | 4/2006 | Davison et al. | |
| 7,056,319 B2 | 6/2006 | Aliperti et al. | |
| 7,135,015 B2 | 11/2006 | Dulak et al. | |
| 7,309,334 B2 | 12/2007 | Von Hoffman | |
| 7,316,677 B1 | 1/2008 | Dulak et al. | |
| 7,329,268 B2 | 2/2008 | Van Nguyen et al. | |
| 7,457,661 B2 | 11/2008 | Doty | |
| 2001/0012950 A1 | 8/2001 | Nishtala et al. | |
| 2001/0037126 A1 | 11/2001 | Stack et al. | |
| 2002/0009535 A1 | 1/2002 | Michal et al. | |
| 2002/0010440 A1 | 1/2002 | Segesser | |
| 2002/0010476 A1 | 1/2002 | Mulholland et al. | |
| 2002/0077653 A1 | 6/2002 | Hudson et al. | |
| 2002/0099431 A1 | 7/2002 | Armstrong et al. | |
| 2002/0161377 A1 | 10/2002 | Rabkin | |
| 2003/0050600 A1 | 3/2003 | Ressemann et al. | |
| 2003/0065353 A1 | 4/2003 | Horzewski et al. | |
| 2003/0135156 A1 | 7/2003 | Bencini et al. | |
| 2003/0195551 A1 | 10/2003 | Davison et al. | |
| 2003/0212384 A1 | 11/2003 | Hayeden | |
| 2003/0216770 A1 | 11/2003 | Persidsky et al. | |
| 2003/0233115 A1* | 12/2003 | Eversull | A61B 17/3431 606/194 |
| 2004/0006344 A1 | 1/2004 | Nguyen et al. | |
| 2004/0073286 A1 | 4/2004 | Armstrong et al. | |
| 2004/0087968 A1 | 5/2004 | Core | |
| 2004/0181273 A1 | 9/2004 | Brasington et al. | |
| 2004/0220549 A1 | 11/2004 | Dittman et al. | |
| 2004/0236346 A1 | 11/2004 | Parker | |
| 2005/0043780 A1 | 2/2005 | Gifford et al. | |
| 2005/0085842 A1 | 4/2005 | Eversull et al. | |
| 2005/0124937 A1 | 6/2005 | Kick et al. | |
| 2005/0125021 A1 | 6/2005 | Nance et al. | |
| 2005/0149105 A1 | 7/2005 | Leeflang et al. | |
| 2005/0222576 A1 | 10/2005 | Kick et al. | |
| 2006/0036276 A1 | 2/2006 | Nguyen et al. | |
| 2006/0052750 A1 | 3/2006 | Lenker et al. | |
| 2006/0142795 A1 | 6/2006 | Nguyen et al. | |
| 2006/0200188 A1 | 9/2006 | Nance et al. | |
| 2006/0200189 A1 | 9/2006 | Nance et al. | |
| 2006/0247602 A1 | 11/2006 | Dulak et al. | |
| 2007/0112335 A1 | 5/2007 | Dulak et al. | |

FOREIGN PATENT DOCUMENTS

| | | |
|---|---|---|
| EP | 024945611 | 12/1987 |
| EP | 0385920 | 9/1990 |
| EP | 0206553 | 1/1991 |
| EP | 0421650 | 4/1991 |
| EP | 0546766 | 6/1993 |
| WO | WO1992/019312 | 11/1992 |
| WO | WO1995/030374 | 11/1995 |
| WO | WO1999/016499 A1 | 4/1999 |
| WO | WO1999/017665 | 4/1999 |
| WO | WO2003/090834 A2 | 11/2003 |

OTHER PUBLICATIONS

United States Patent and Trademark Office, Examiner's Answer dated Jun. 21, 2012 in U.S. Appl. No. 10/y28,728, 13 pages.

United States Patent and Trademark Office, Final Office Action dated Jul. 22, 2011 in U.S. Appl. No. 10/728,728, 13 pages.

European Patent Office, Communication in European Application No. 04813043.9 filed on Dec. 3, 2004.

United States Patent and Trademark Office, Office Action dated Oct. 29, 2010 in U.S. Appl. No. 10/728,728, 14 pages.

United States Patent and Trademark Office, Final Office Action dated Mar. 22, 2010 in U.S. Appl. No. 10/728,728, 17 pages.

United States Patent and Trademark Office, Office Action dated Mar. 19, 2010 in U.S. Appl. No. 11/415,764.

United States Patent and Trademark Office, Response dated Oct. 16, 2009 to Non-final Rejection in U.S. Appl. No. 11/884,017.

United States Patent and Trademark Office, Response dated Sep. 15, 2009 to Office Action in U.S. Appl. No. 11/223,897.

United States Patent and Trademark Office, Office Action dated Jul. 23, 2009 in U.S. Appl. No. 10/728,728, 15 pages.

United States Patent and Trademark Office, Office Action dated Jul. 22, 2009 in U.S. Appl. No. 11/415,659.

United States Patent and Trademark Office, Final Office Action dated Jun. 30, 2009 in U.S. Appl. No. 11/415,764.

European Patent Office, Communication dated May 25, 2009 in European Patent Application No. 04813043.9.

United States Patent and Trademark Office, Response dated May 12, 2009 to Final Office Action in U.S. Appl. No. 11/223,897.

United States Patent and Trademark Office, Response dated May 11, 2009 to Final Office Action in U.S. Appl. No. 11/415,659.

United States Patent and Trademark Office, Office Action dated Apr. 17, 2009 in U.S. Appl. No. 11/884,017.

United States Patent and Trademark Office, Final Office Action dated Apr. 17, 2009 in U.S. Appl. No. 11/223,897.

United States Patent and Trademark Office, Final Office Action dated Apr. 6, 2009 in U.S. Appl. No. 11/415,659.

United States Patent and Trademark Office, Response dated Mar. 2, 2009 in U.S. Appl. No. 11/884,017.

United States Patent and Trademark Office, Final Office Action dated Feb. 19, 2009 in U.S. Appl. No. 10/728,728, 10 pages.

United States Patent and Trademark Office, Restriction Requirement dated Feb. 5, 2009 in U.S. Appl. No. 11/884,017.

United States Patent and Trademark Office, Response dated Feb. 3, 2009 to Office Action in U.S. Appl. No. 11/223,897.

European Patent Office, Response dated Jan. 15, 2009 to Jul. 14, 2008 Communication in European Application No. 05794899.4.

United States Patent and Trademark Office, Response dated Dec. 12, 2008 to Office Action in U.S. Appl. No. 11/415,764.

United States Patent and Trademark Office, Response dated Nov. 19, 2008 to Office Action in U.S. Appl. No. 11/415,659.

United States Patent and Trademark Office, Office Action dated Oct. 3, 2008 in U.S. Appl. No. 11/223,897.

European Patent Office, Response dated Aug. 11, 2008 to European Patent Office Communication dated Jan. 30, 2008 in European Patent Application No. 04813043.9.

European Patent Office, Communication dated Jul. 14, 2008 in European Patent Application No. 05794899.4

United States Patent and Trademark Office, Office Action dated Jun. 13, 2008 in U.S. Appl. No. 11/415,764.

United States Patent and Trademark Office, Office Action dated May 28, 2009 in U.S. Appl. No. 10/728,728, 20 pages.

United States Patent and Trademark Office, Office Action dated May 20, 2008 in U.S. Appl. No. 11/415,659.

United States Patent and Trademark Office, Response dated Feb. 20, 2008 to Final Office Action in U.S. Appl. No. 11/415,659.

United States Patent and Trademark Office, Response dated Feb. 20, 2008 to Office Action in U.S. Appl. No. 11/415,764.

(56) References Cited

OTHER PUBLICATIONS

European Patent Office, Communication dated Jan. 30, 2008 in European Patent Application No. 04813043.9.
United States Patent and Trademark Office, Advisory Action dated Nov. 16, 2007 in U.S. Appl. No. 11/415,659.
United States Patent and Trademark Office, Response dated Nov. 7, 2007 to Final Office Action in U.S. Appl. No. 11/415,659.
United States Patent and Trademark Office, Office Action dated Oct. 18, 2007 in U.S. Appl. No. 10/728,728, 9 pages.
European Patent Office, Examination Report dated Aug. 21, 2007 in European Patent Application No. 05794899.4.
United States Patent and Trademark Office, Final Office Action dated Aug. 20, 2007 in U.S. Appl. No. 11/415,659.
United States Patent and Trademark Office, Office Action dated Aug. 20, 2007 in U.S. Appl. No. 11/415,764.
United States Patent and Trademark Office, Response dated Jun. 11, 2007 to Office Action in U.S. Appl. No. 11/415,659.
United States Patent and Trademark Office, Response dated Jun. 8, 2007 to Office Action in U.S. Appl. No. 11/415,764.
United States Patent and Trademark Office, Notice of Allowance dated May 1, 2007 in U.S. Appl. No. 10/728,728, 11 pages.
WIPO, U.S. International Search Authority, International Search Report dated Apr. 3, 2007 in International Patent Application No. PCT/US2005/031958.
United States Patent and Trademark Office, Office Action dated Jan. 10, 2007 in U.S. Appl. No. 11/415,659.
United States Patent and Trademark Office, Office Action dated Jan. 8, 2007 in U.S. Appl. No. 11/415,764.
United States Patent and Trademark Office, Office Action dated Sep. 13, 2006 in U.S. Appl. No. 10/728,728, 14 pages.
United States Patent and Trademark Office, prosecution history in U.S. Patent Publication No. 2006/0200188 published Sep. 7, 2006.
United States Patent and Trademark Office, prosecution history in U.S. Patent Publication No. 2006/0200189 published Sep. 7, 2006.
WIPO, International Preliminary Examining Authority (U.S. Patent and Trademark Office), International Preliminary Report on Patentability dated Jun. 15, 2006 in International Patent Application No. PCT/US2004/040651.
WIPO, U.S. International Search Authority, International Search Report dated Jun. 7, 2006 in International Patent Application No. PCT/US2004/040651.
WIPO, U.S. International Search Authority, International Search Report dated Oct. 28, 2005 in International Patent Application No. PCT/US2004/040651.
United States Patent and Trademark Office, prosecution history in U.S. Patent Publication No. 2005/0125021 published Jun. 9, 2005.
United States Patent and Trademark Office, Office Action dated Jun. 30, 2009 in U.S. Appl. No. 11/223,897.

* cited by examiner

EXPANDABLE PERCUTANEOUS SHEATH

RELATED APPLICATIONS

This application claims priority to U.S. patent application Ser. No. 10/728,728 filed Dec. 5, 2003 entitled Expandable Percutaneous Sheath, which is hereby incorporated herein by reference in its entirety.

BACKGROUND OF THE INVENTION

Field of the Invention

The present invention relates to medical devices and, more particularly, to methods and devices for forming a percutaneous channel. In one application, the present invention relates to methods and devices for providing percutaneous access to a soft tissue or organ.

Description of the Related Art

A wide variety of diagnostic or therapeutic procedures involve the introduction of a device through a natural or artificially created access pathway. A general objective of access systems, which have been developed for this purpose, is to minimize the cross-sectional area of the puncture, while maximizing the available space for the diagnostic or therapeutic instrument. These procedures include, among others, a wide variety of laprascopic diagnostic and therapeutic interventional procedures.

Percutaneous nephrostomy is an example of one type of therapeutic interventional procedure that requires an artificially created pathway. Percutaneous nephrostomy is a minimally invasive procedure that can be used to provide percutaneous access to the upper urinary tract. At first, percutaneous nephrostomy was used only for urinary diversion but now it may be used for more complex procedures such as stone extraction, integrate endopyelotomy, and resection of transitional cell carcinoma of the upper urinary tract.

In many percutaneous nephrostomy systems, a stiff guidewire is first placed into the renal collection system through the renal parenchyma and the ureter using fluoroscopic control. A second "safety wire" may be placed with a dual lumen catheter for maintaining the tract should the first wire become dislodged or kinked.

Once guidewire control is established, a dilator sheath is used to create the tract and establish a rigid working lumen. An early technique involved advancing a flexible, 8 French, tapered catheter over the first guidewire to provide guidewire protection as well as a stable path for the placement of larger diameter dilators and sheaths. The larger diameter sheaths are sequentially advanced over the catheter and each other until an approximately 34 French tract is established. The inner sheaths or dilators may then be sequentially removed such that the outermost sheath defines a working lumen. In this system, tract formation is accomplished by the angular shearing force of each subsequent sheath placement, which cuts a path through the tissue. Because axial pressure is required to advance and place each sheath, care must be taken to avoid kinking the tapered catheter and/or advancing the sheaths to far and perforating the renal pelvis. This technique also requires a large number of steps.

A more recent technique utilizes a balloon that is advanced over the first guide wire. Once in place in the renal pelvis, the balloon is inflated with a dilute contrast media solution to enlarge the tract. Once the balloon is inflated to a suitable diameter, a rigid sheath is advanced over the balloon. Advancing the rigid sheath over the balloon typically requires applying axial force to the sheath and rotation. The balloon may then be deflated and removed from the rigid sheath so that the rigid sheath may define a working lumen. In general, this technique is considered less traumatic than the previously described technique. Nevertheless, placement of the rigid sheath still involves angular shearing forces and several steps.

Additional information regarding percutaneous nephrostomy can be found in McDougall, E. M., et al. (2002), Percutaneous Approaches to the Upper Urinary Tract, *Campbell's Urology*. 8th ed, vol. 4, pp. 3320-3357, Chapter 98. Philadelphia, Saunders.

A need therefore remains for improved access technology which allows a device to be percutaneously passed through a small diameter tissue tract, while accommodating the introduction of relatively large diameter instruments.

SUMMARY OF THE INVENTION

A percutaneous access sheath is provided according to an embodiment of the present invention. In one application, the percutaneous access sheath is used to provide access to the upper urinary tract or bladder.

In one embodiment, the percutaneous access sheath may be used in conjunction with a deployment catheter, which may be provided with a balloon at its distal end. The percutaneous access sheath has a proximal section and a variable diameter distal section. The deployment catheter may be disposed within the percutaneous access sheath such that the balloon is positioned within the distal section of the percutaneous access sheath.

In one embodiment, the distal section of the percutaneous access sheath is restrained in a first, small diameter by a releasable restraint such as a perforated, scored or thin wall continuos film insert jacket. The distal section of the percutaneous access sheath is creased by at least 2 to 4 or 2 to 6 folds and inserted into a distal section of the jacket. This gives the percutaneous access sheath a smaller cross-sectional profile, facilitating its insertion.

In one embodiment, the folded percutaneous access sheath is restrained within the jacket. Following insertion into a patient's anatomy, the jacket may be released by inflating the balloon on the deployment catheter. During the inflation process, the jacket separates along its longitudinal axis as the access sheath unfolds and/or expands. In one preferred embodiment, separation of the jacket during inflation, occurs along a perforated or scored line formed on the jacket. In one such embodiment, the score or perforation may be formed at or close to the distal end of the jacket such that the jacket separates at the distal end first. In another preferred embodiment, the jacket is formed from a continuous film and the separation is caused by stretching the film until it separates. After the balloon has expanded the access sheath to its full diameter and caused the jacket to separate, the jacket may be withdrawn from the patient's anatomy. In a modified embodiment, the jacket may remain coupled to the access sheath during use. The balloon may be deflated to allow the removal of the deployment catheter, leaving the percutaneous access sheath in place.

In one embodiment where the percutaneous access sheath is used to provide access to the upper urinary tract, the percutaneous access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder Other applications of the percutaneous access sheath include a variety of diagnostic or therapeutic clinical situations which require access to the inside of the body, through either an artificially created or natural body lumen.

DETAILED DESCRIPTION OF THE PREFERRED EMBODIMENT

Figure 1:
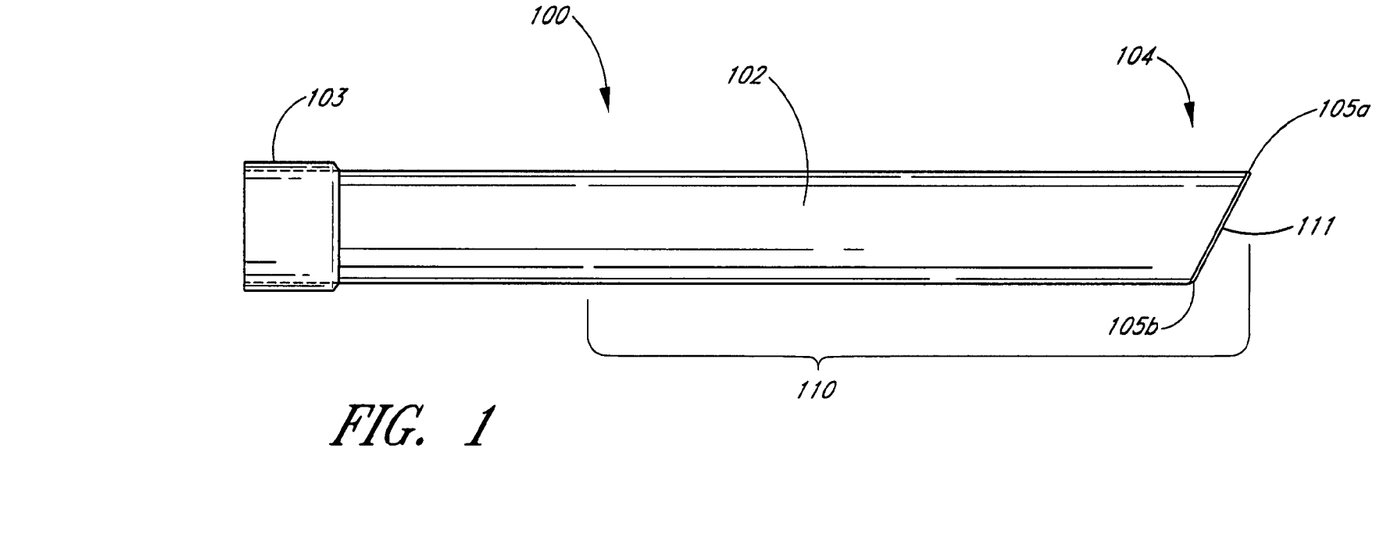
FIG. 1 is a side elevational view of a percutaneous access sheath.
Figure 1A:
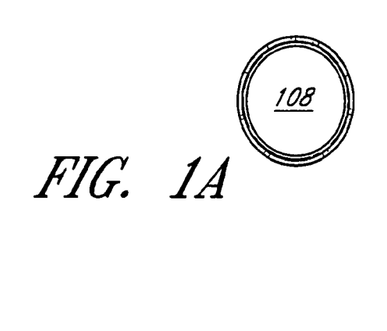
FIG. 1A is a front view of the percutaneous access sheath.

FIG. 1 is an overview of an exemplary embodiment of a percutaneous access sheath 100. The sheath 100 generally comprises an elongate tubular body 102 with an axial lumen 108 (FIG. 1A), and is designed to provide percutaneous access to a diagnostic or treatment site in the body.

In the exemplary embodiment, the elongate tubular body 102 has a distal section 110 and a proximal section 103. The proximal section 103 has a slightly larger inner and outer diameter as compared to the distal section 110. As will be explained in more detail below, the proximal section 103 may be used to secure the access sheath 100 to a connector. With continued reference to FIG. 1, the distal end 104 of the distal section 110 may be provided with a beveled distal face 111, which preferably forms an angle of about 45 to about 75 degrees with respect a longitudinal axis of the tubular body 102. In this manner, the distal face 111 forms a leading edge 105a and a trailing edge 105b. As will be explained below, during insertion, the beveled face 111 advantageously provides the distal end 104 of the access sheath 100 with a smaller cross-sectional profile in a compressed configuration. This provides a smoother transition from the distal end 104 of the access sheath 100 to the deployment catheter (described below). In addition, in the expanded configuration, the leading edge 105a maintains positional purchase within the target tissue or organ while the trailing edge 105b provides the sheath 100 with an aperture to facilitate instrument maneuvering and visualization within the internal structure of the tissue or organ under examination or treatment. In a modified embodiment, the distal face 111 may be form an angle of about 90 degrees with respect to the longitudinal axis of the tubular body.

The length and diameter of the sheath 100 can be varied according to clinical need, as will be understood by those skilled in the art with reference to this disclosure. In one exemplary embodiment for percutaneous nephrostomy, the access sheath 100 has an overall length of about 17 to about 30 centimeters with the distal section 110 having a length of about 11 to about 24 centimeters. As will be explained in more detail below, a portion or all of the distal section 110 is expandable from a first, smaller cross-sectional profile to a second, larger cross-sectional profile. The first, smaller cross-sectional profile of the distal section 110 eases its insertion into a percutaneous treatment site. After insertion, the distal section 110 is expanded to a second, larger cross-sectional profile to provide a larger passageway for surgical instruments to reach the percutaneous treatment site. For percutaneous nephrostomy, the smaller cross-sectional profile may have a diameter of about 15 French to about 24 French and the larger cross-sectional profile may have a diameter of about 21 French to about 40 French. In the larger cross-sectional profile, the lumen 108 may have a diameter of about 18 French to about 38 French.

As mentioned above, in the illustrated embodiment, the percutaneous access sheath 100 comprises a tubing 102, which defines a lumen 108. The tubing 102 may be made of PTFE, nylon, PEBAX or polyethylene, polyurethane, silicone, or other suitable materials.

In this embodiment, the distal section 110 is creased in at least two and more preferably 2 to 6 sections, most preferably 2 to 4 sections, and collapsed from a larger to a smaller cross-sectional profile to ease its insertion. As discussed below, in one embodiment for percutaneous nephrostomy, the distal section 110 is placed into the renal collecting system through the renal parenchyma and ureters. Its length is thus determined by the anatomy and is generally in the range of about 11 cm to about 24 cm. In the illustrated embodiment, the proximal end 103 of the tubing 102 is flared and fitted onto the deployment catheter as will be explained below. The overall length of the tubing 102 depends on the distance between the insertion and treatment locations, and is generally in the range of 10-100 cm for various clinical indications. As mentioned above, for percutaneous nephrostomy, the length of the tubing is approximately 17-30 cm.

Figure 2:
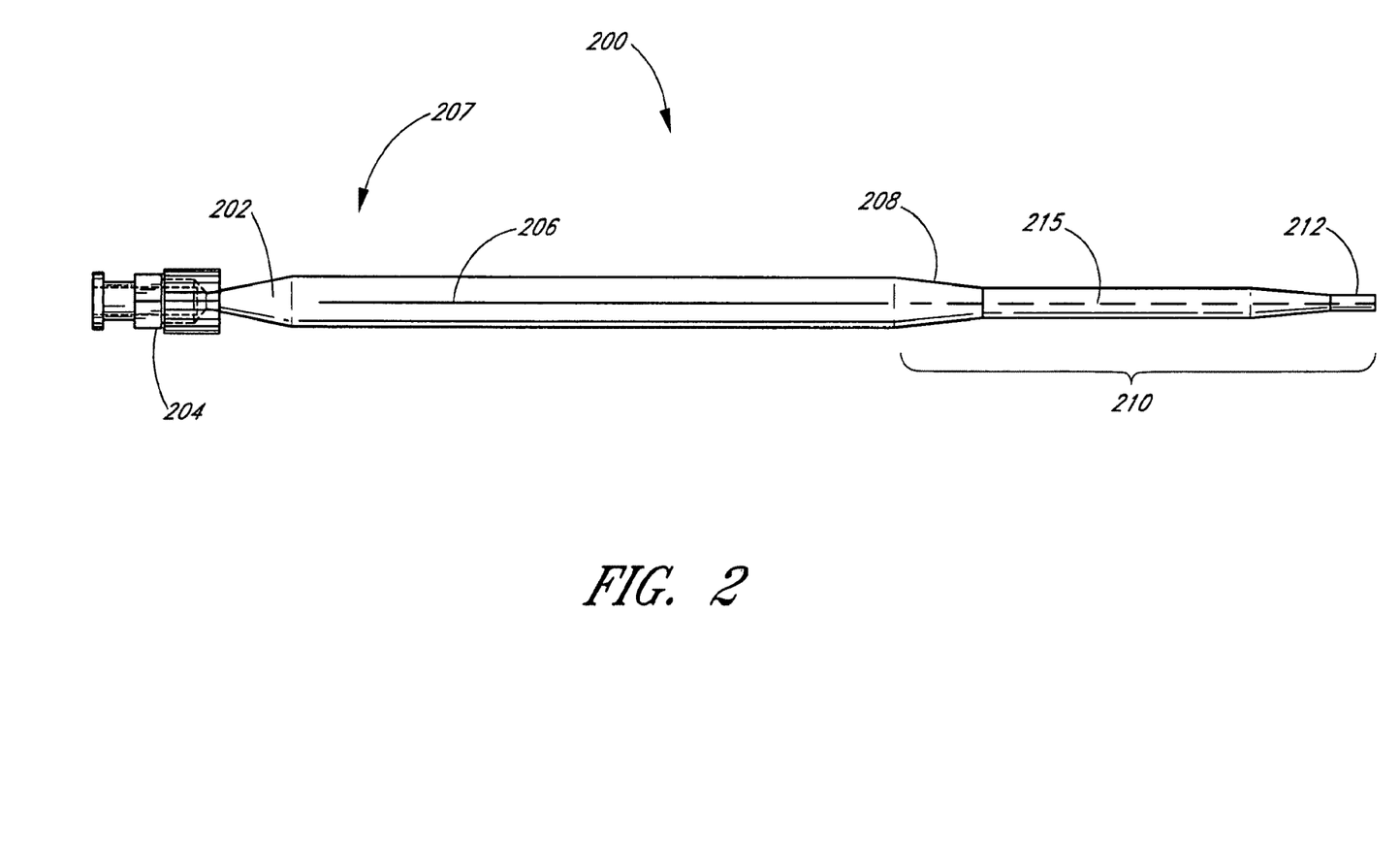
FIG. 2 is a side elevational view of a jacket.

FIG. 2 is an overview of the jacket 200. It is preferably made of a thin, smooth and flexible material. The jacket 200 has a proximal section 207 and a distal, restraint section 210. The restraint section 210 has a smaller cross-sectional profile than the proximal section 207 of the jacket 200. The restraint section 210 is adapted to restrain a portion or all of the distal section 110 of the percutaneous access sheath 100 in a smaller cross-sectional profile. This is achieved by constraining the percutaneous access sheath 100 in the jacket 200 such that all or a portion of the distal section 110 of the percutaneous access sheath 100 lies within the restraint section 210 of the jacket 200.

In the illustrated embodiment, the jacket 200 may be made of heat shrink PTFE. The proximal end 202 of the jacket 200 terminates at a pull tab 204, which may be formed by any of a variety of structures such as a threaded connector with a luer lock at its proximal end. The jacket 200 may be provided with a slit 206 near its proximal end 202. The jacket 200 tapers at a first tapering point 208 into a restraint section 210, which tapers again into the distal tip 212. As discussed above, the restraint section 210 restrains the distal section 110 of the percutaneous access sheath 100 in its smaller cross-sectional profile. Thus the length of the restraint section 210 is approximately the same as or slightly longer or shorter than the distal section 110, and generally falls in the range of about 1 1-25 cm.

The outside diameter of the restraint section 210 is preferably configured to ease its insertion into a percutaneous treatment site. Depending upon the clinical application, the outside diameter may be in the range of about 3 French to about 40 French. For percutaneous nephrostomy, the outside diameter may be in the range of about 5 French to about 35 French. The restraint section 210 is configured to separate and/or tear preferably along its longitudinal axis to release the access sheath 100 as it is radially expanded. In the illustrated embodiment, the jacket 200 is perforated, scored or otherwise provided with a tear line 215 from the first tapering point 208 to its distal tip 212. In another embodiment, the jacket 200 may be constructed of a material that will disrupt or separate during expansion from the first tapering point 208 to its distal tip 212. In another embodiment, the jacket 200 may be perforated, scored or otherwise provided with a tear line for only a portion of the restraint section 210. For example, in one embodiment, the restraint section 210 may be provided with a tear line at a region close to or at the distal end of the jacket 200. This may cause the jacket 200 to disrupt or separate during expansion from its distal end first The distance between the slit 206 and the distal tip 212 is generally approximately equal to or longer than the length of the folded, compressed portion of the tubing 102 such that the folded compressed portion of the tubing 102 terminates within the restraint section 210. In one embodiment, this arrangement permits complete disruption of the jacket 200 when the access sheath 100 is fully expanded. In one embodiment, the distance between the slit 206 and the distal tip 212 is generally in the range of 6-90 cm for most clinical applications and about 11-24 cm for percutaneous nephrostomy. In the illustrated embodiment, which is configured for percutaneous nephrostomy, this distance is approximately 1 1cm, and the overall length of the jacket 200 is approximately 19 cm.

Figure 3:
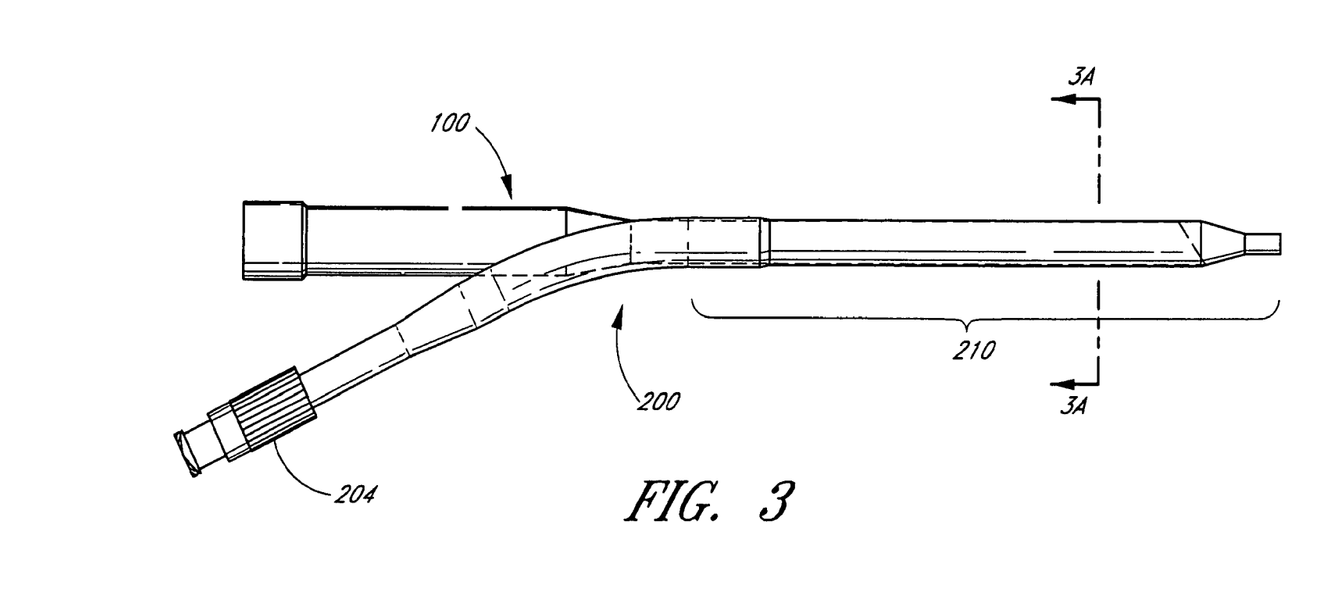
FIG. 3 illustrates the percutaneous access sheath in a reduced cross-sectional configuration and inserted into the jacket.

FIG. 3 illustrates the percutaneous access sheath 100 inserted into the jacket 200 via the slit 206 provided near its proximal end 202. The diameter of the restraint section 210 of the jacket 200 is smaller than the diameter of the distal section 110 of the tubing 102. In the illustrated embodiment, the distal section 110 is creased and folded inwards to decrease its effective diameter, and inserted into the restraint section 210. As discussed above, the restraint section 210 restrains the distal section 110 of the percutaneous access sheath 100 in its smaller cross-sectional profile. The restraint section 210 may be approximately the same length as or shorter than the distal section 110. In the illustrated embodiment, the restraint section 210 is approximately 11-24 cm.

As will be explained in more detail below, in some embodiments, the jacket 200 is removed from the access sheath 100 and the surgical site after the sheath 100 is expanded. In other embodiments, the jacket 200 is attached to the sheath 100 and remains attached to the sheath 100 after it is expanded and during the surgical procedure. In such latter embodiments, the jacket 200 may be securely attached to the access sheath by, for example, at least one adhesive or heat bond, preferably extending axially along a section of the access sheath 100 generally opposite the folds or creases.

In certain embodiments a jacket 200 may not be necessary if the distal section 110 of the percutaneous access sheath 100 is made of a stretchable material that may be stretched from a first, smaller cross-sectional profile to a second, larger cross-sectional profile. In these embodiments the outer surface of the distal section 110 is preferably made of a smooth material to facilitate the insertion of the percutaneous access sheath 100 into a treatment site. In still other embodiments, the jacket 200 may be a stretchable material that may be stretched with or without elastic deformation from a first, smaller cross-sectional profile to a second, larger cross-sectional profile as the sheath is expanded.

Figure 4:
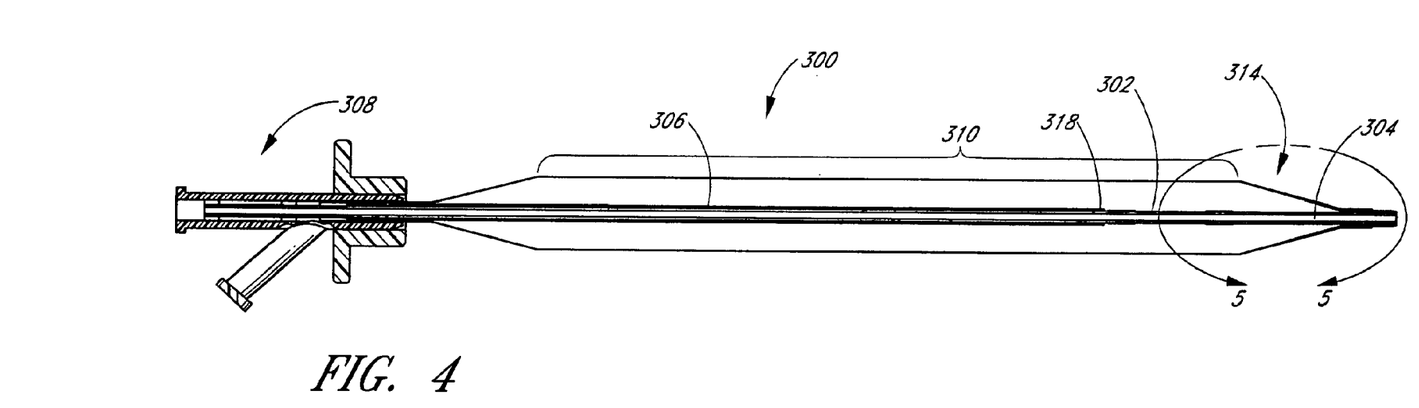
FIG. 4 is a side elevational view of an access sheath expansion balloon catheter.

FIG. 4 is an overview of the deployment catheter 300. It is provided with an expansion element such as balloon 310. As will be explained in more detail below, the deployment catheter 300 is inserted into the lumen 108 of the percutaneous access sheath 100 such that the balloon 310 is arranged within the distal section 110. The balloon 310 may then be inflated to expand the distal section 110 from its first, smaller cross-sectional profile to its second, larger cross-sectional profile following the insertion of the percutaneous access sheath 100 into a treatment site.

With particular reference to FIG. 4, an inner tube 302 extends the entire length of the deployment catheter 300. A guide wire lumen 304 is defined by the interior of the inner tube 302. The deployment catheter 300 can travel along a guide wire extending through the guide wire lumen 304. The inner tube 302 carries coaxially on its exterior an outer tube 306. The outer tube 306 terminates proximally into the distal end of a y-connector 308, and distally into a balloon 310. The balloon 310 may be made of PET. The y-connector 308 may be provided with an optional support tube (not shown) extending from its distal end and over a proximal section of the outer tube 306, to increase the rigidity of the deployment catheter 300 during insertion. This support tube may be made of any of a variety of materials, such as, a stainless steel hypotube.

Figure 5:
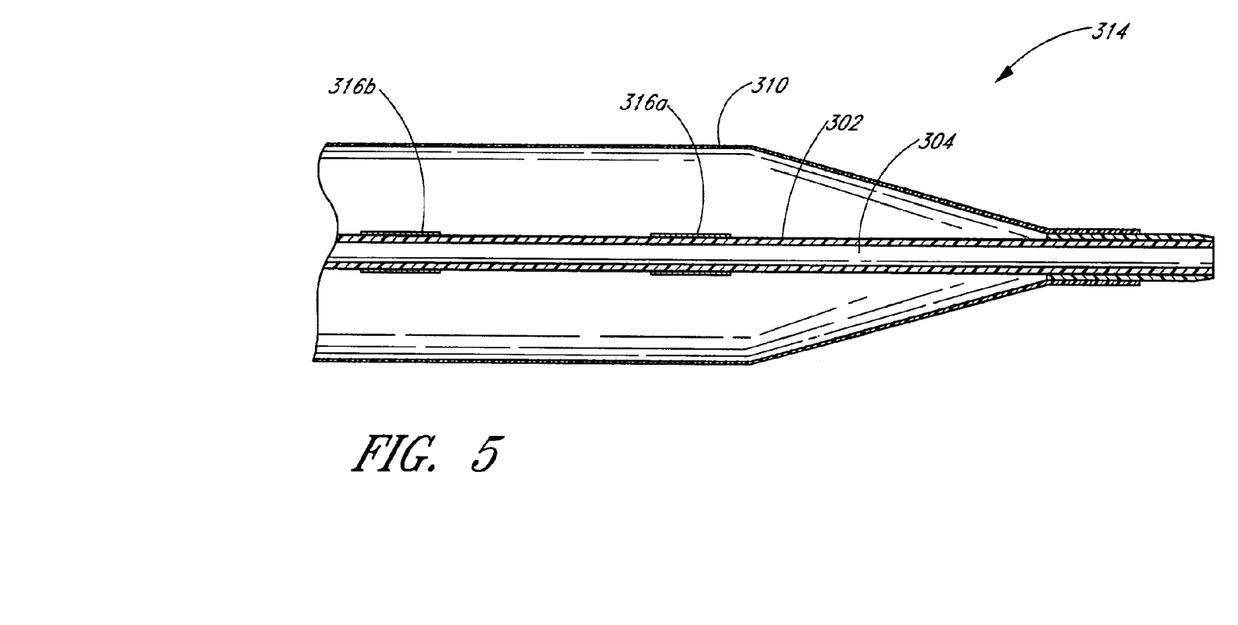
FIG. 5 is an enlarged view of the distal end of the expansion balloon catheter.
Figure 8:
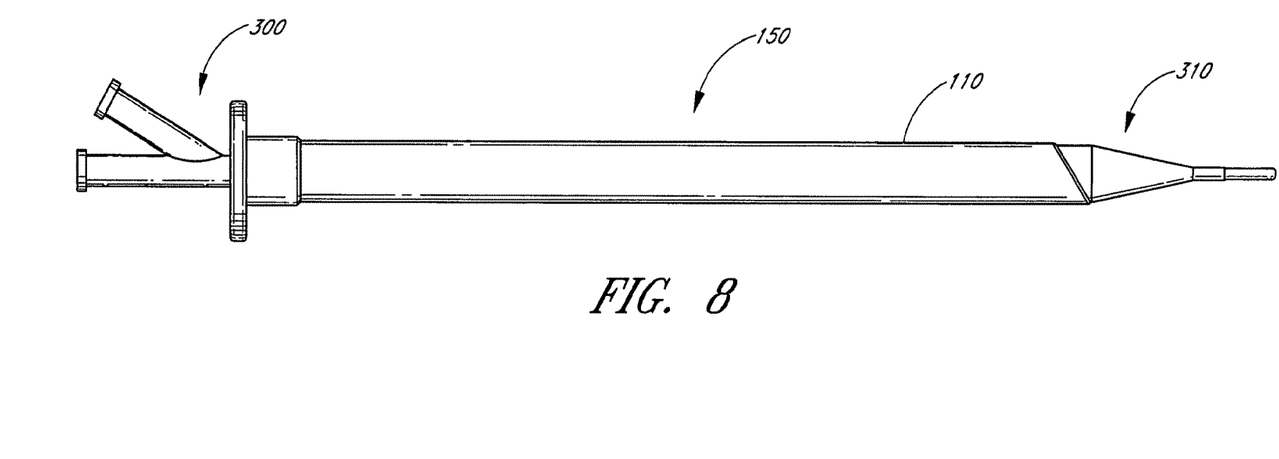
FIG. 8 illustrates the percutaneous access sheath assembly of FIG. 7 in an expanded configuration and the jacket removed.

FIG. 5 is an enlarged view of the distal end 314 of the exemplary embodiment of the deployment catheter 300. Both the inner tube 302 and the guide wire lumen 304 extend through the distal end 314 of the balloon 310. The inner tube 302 may carry coaxially on its exterior a pair of marker rings 316a, 316b near the distal end 314 of the balloon 310. With reference to FIG. 8, the pair of markers 316a, 316b are spaced apart such that when the deployment catheter 300 is inserted into the lumen 108 and expanded they correspond to the distal edge 105a and proximal edge 105b of the beveled distal face 111 (see FIG. 1). In a modified arrangement, the markers 316a, 316b may be carried by the distal end 314 of the balloon 310. The markers 316a,b ma be made of gold, tantalum, platinum or another radio-opaque material. Additional markers may be provided on the deployment catheter to aid in visualizing its location. In another embodiment, the markers 316a, 316b may be replaced with a single axially elongated marker having a leading and trailing edge that corresponds to the distal edge 105a and proximal edge 105b of the beveled distal face 111.

With reference back to FIG. 4, a balloon inflation lumen 318, defined in the space between the inner tube 302 and the outer tube 306, communicates with the interior of the balloon 310. As discussed above, the balloon 310 may be inflated to expand the distal section 110 of the percutaneous access sheath 100 from its first, smaller cross-sectional profile to its second, larger cross-sectional profile. Thus the length of the balloon 310 is approximately equal to or slightly longer than the length of the distal section 110. In the illustrated embodiment, which is configured for percutaneous nephrostomy the length of the balloon 310 is approximately 12.5 cm. For other clinical applications, the length of the balloon 310 may be in the range of about 8-90 cm.

Figure 6:
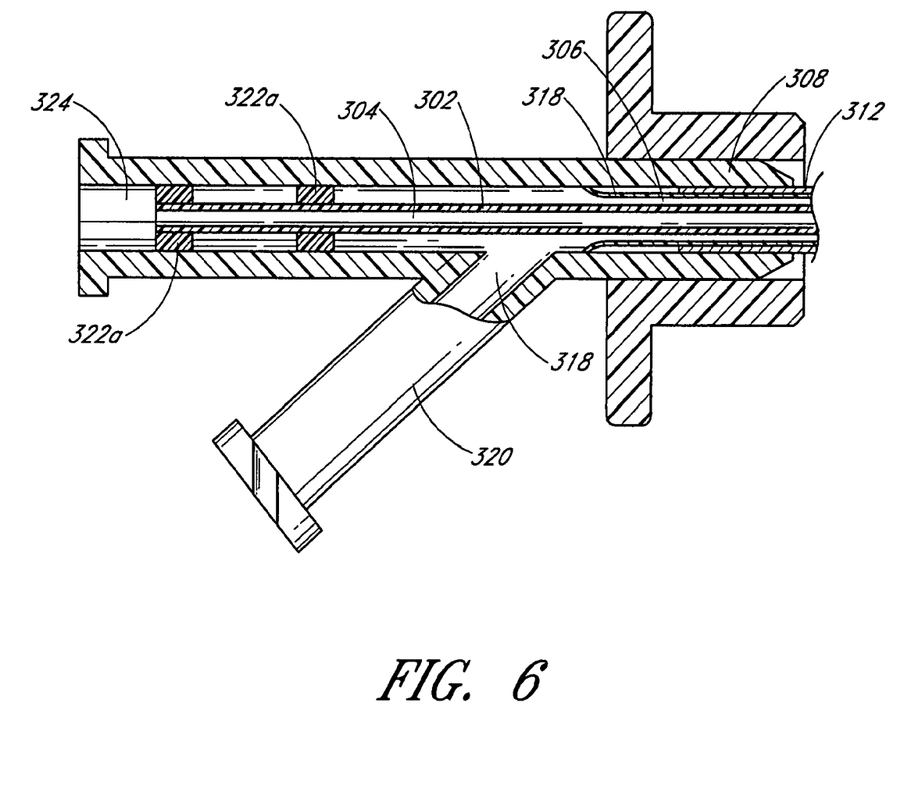
FIG. 6 is an enlarged view of the proximal end of the expansion balloon catheter.

FIG. 6 is an enlarged view of the proximal end of the illustrated embodiment of the deployment catheter 300. Both the inner tube 302 and the guide wire lumen 304 extend through the distal end of the y-connector 308. The balloon inflation lumen 318, defined in the space between the inner tube 302 and the outer tube 306, opens into a port 320 in the y-connector 308. The illustrated embodiment uses a pair of stoppers 322a, 322b to align the inner tube 302 within the y-connector 308 and prevent the balloon inflation lumen 318 from communicating with the space 324 in the main branch of the y-connector 308. Thus only the port 320 communicates via the balloon inflation lumen 318 with the interior of the balloon. A pump may be connected to the port 320 to inflate or deflate the balloon. To enable visualization of the state of the balloon, it may be inflated with contrast media.

Figure 7:
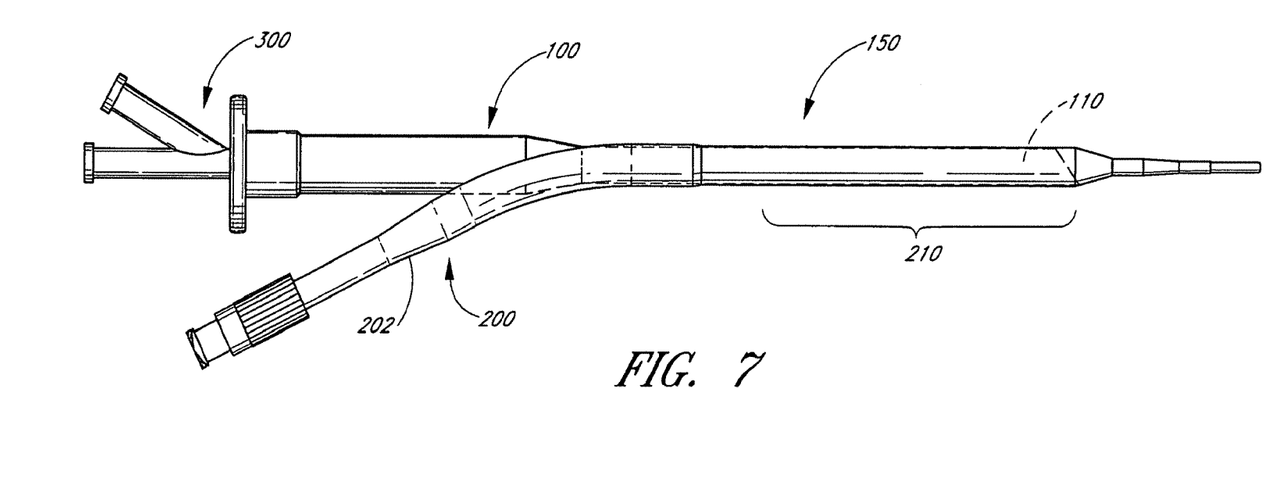
FIG. 7 illustrates the percutaneous access sheath assembly, with the expansion balloon catheter inserted into the structure illustrated in FIG. 3.

FIG. 7 illustrates the percutaneous access sheath assembly 150 in a collapsed or smaller profile configuration. The percutaneous access sheath assembly 150 comprises the percutaneous access sheath 100, the jacket 200 and the deployment catheter 300. It is assembled by inserting the deployment catheter 300 into the percutaneous access sheath 100 and inserting the percutaneous access sheath 100 into the jacket 200 such as via the slit 206 or other proximal opening provided near its proximal end 202. The balloon 310, which is not shown in FIG. 7, of the deployment catheter 300 is deflated, folded and inserted into the distal section 110 of the access sheath 100. The distal section 110, as discussed above, is creased and folded inwards to decrease its effective diameter, and inserted into the restraint section 210 of the jacket 200. As discussed, the balloon 310 is approximately the same length as or just longer than the distal section 110 and the restraint section 210.

FIG. 8 illustrates the percutaneous access sheath assembly 150 in an expanded or larger profile configuration. In the expanded configuration, the jacket 200 has been removed and the balloon 310 has been inflated to expand the distal section 110 of the access sheath 100.

Figure 9:
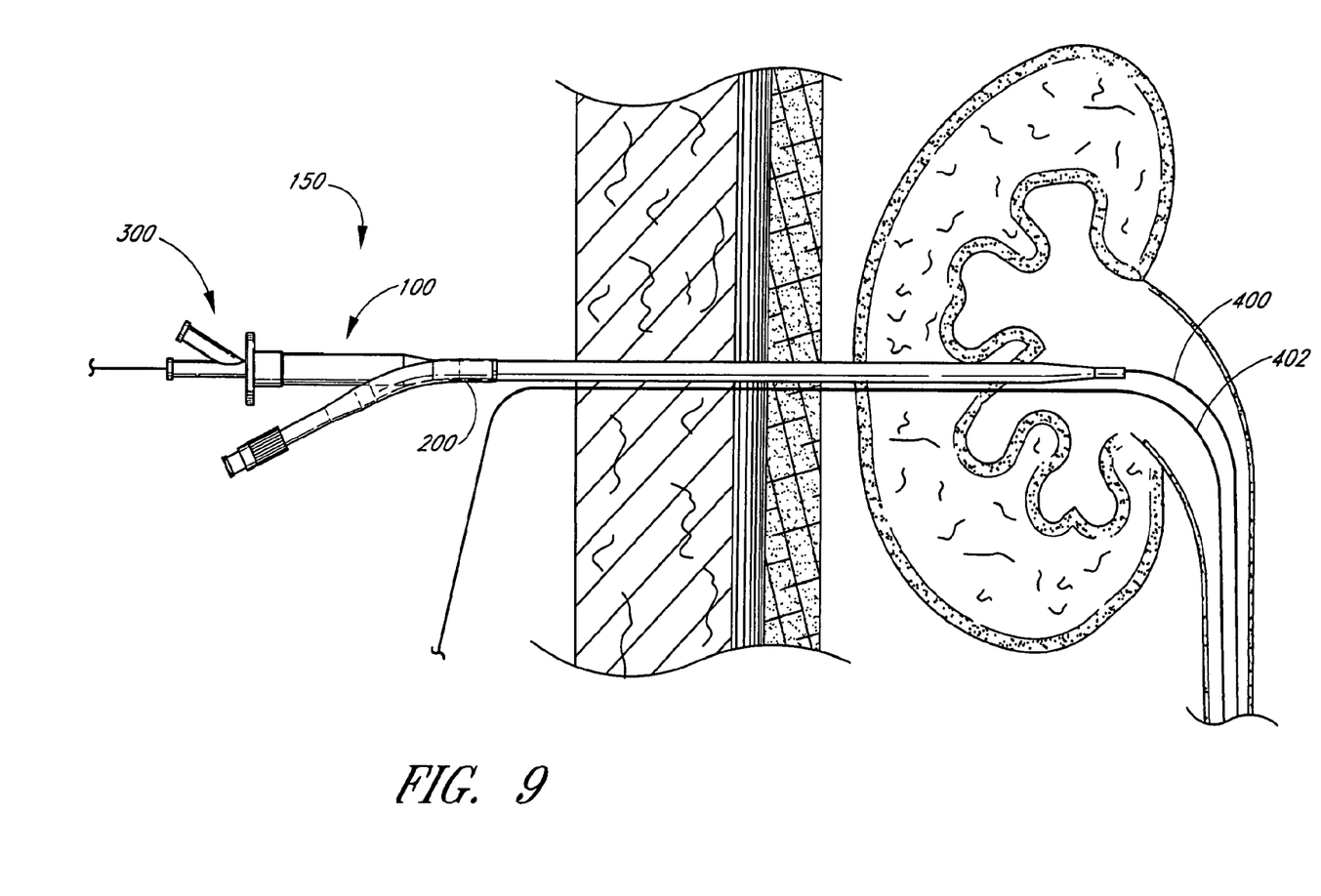
FIG. 9 illustrates the percutaneous access sheath assembly of FIG. 7 inserted into a renal calyx of a kidney, in a first, low profile configuration.
Figure 10:
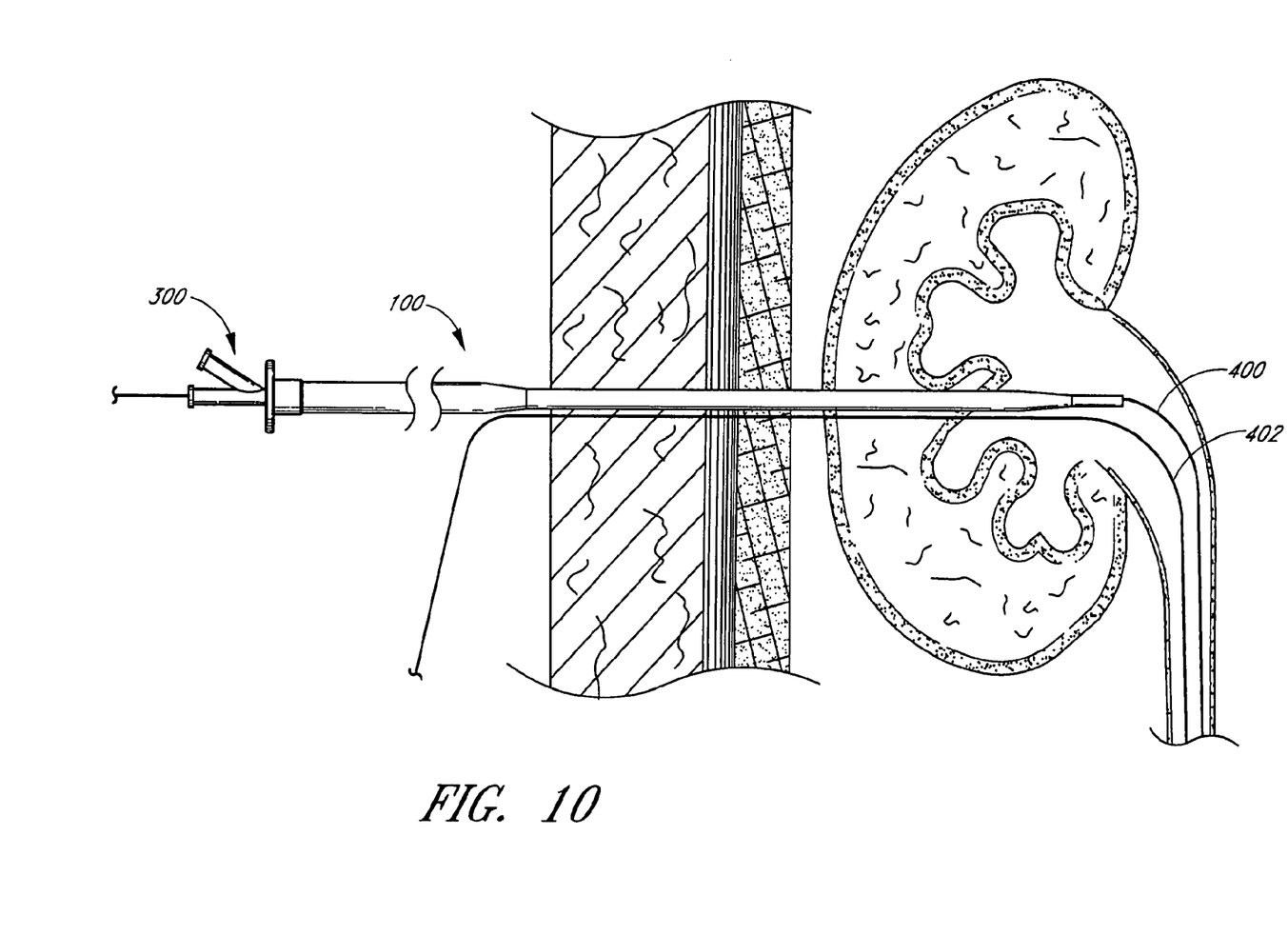
FIG. 10 illustrates the percutaneous access sheath assembly of FIG. 9 with the jacket removed.
Figure 11:
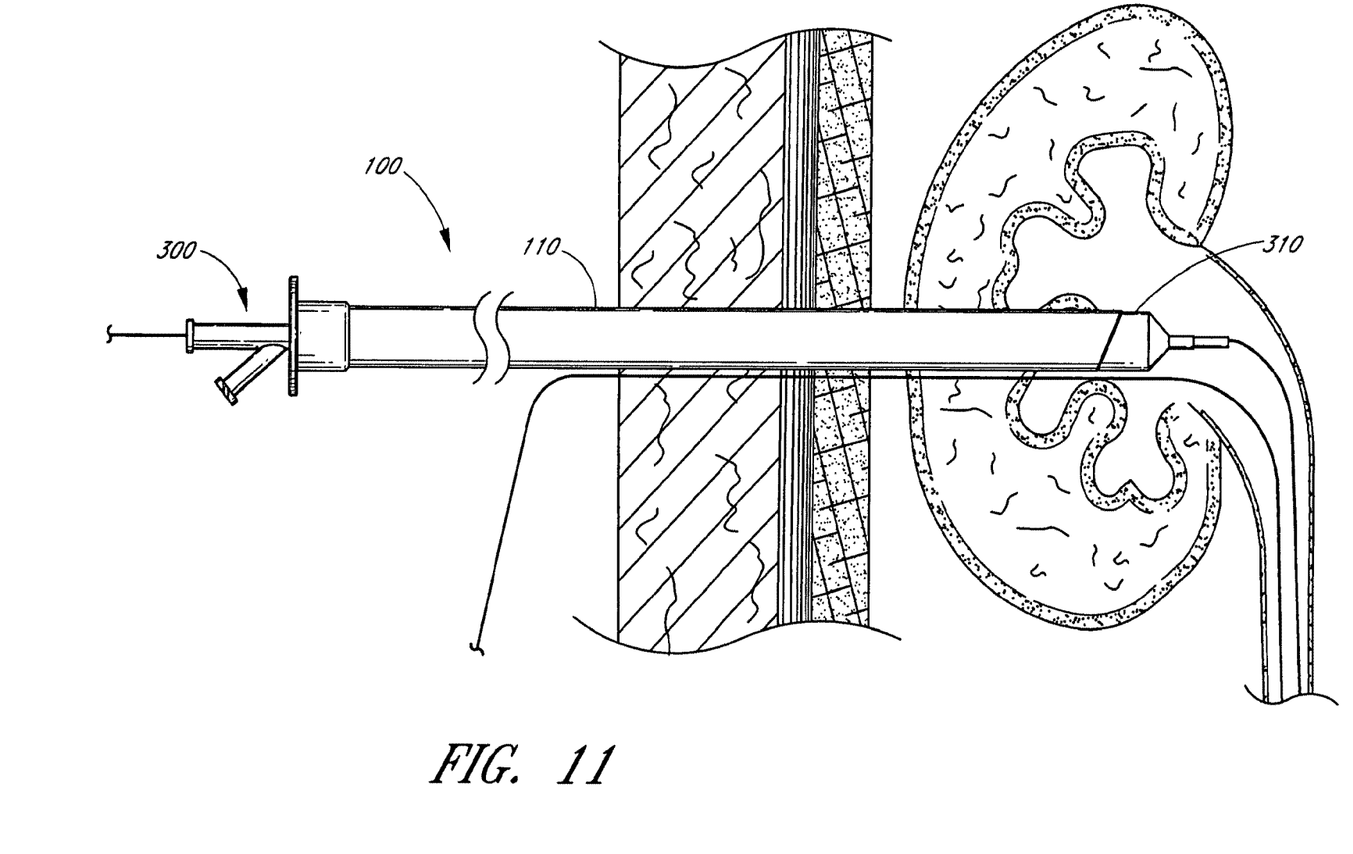
FIG. 11 illustrates the percutaneous access sheath assembly of FIG. 10 with the jacket removed and the expansion catheter fully expanded in a second, functional configuration.
Figure 12:
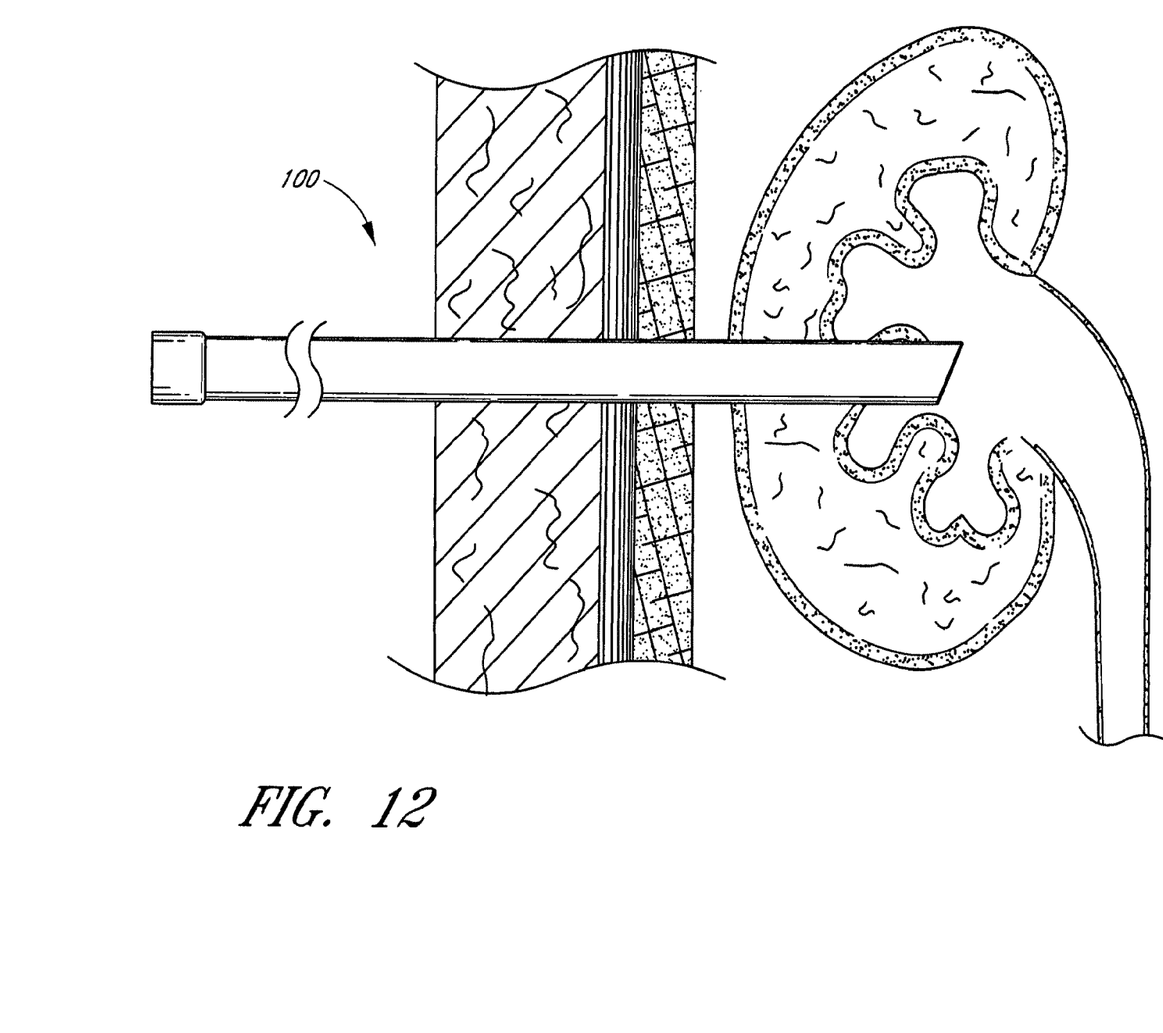
FIG. 12 illustrates the percutaneous access assembly of FIG. 11 with the expansion catheter removed.

One exemplary embodiment of use will now be described with reference to FIGS. 9-12. As shown in FIG. 9, a guidewire 400 may be placed into the renal collection system. In one embodiment, the guidewire 400 is inserted through the renal parenchyma and the ureter using fluoroscopic control. The guidewire 400 may be 0.038" stiff guidewire that is inserted through a small (e.g., 1.7 to two centimeter) incision made at the guidewire skin entry cite. A second "safety wire" 402 may be placed with a dual lumen catheter (not shown) for maintaining the tract should the first wire become dislodged or kinked.

The guide wire 400 may be inserted into the guide wire lumen 304 (see FIG. 4) of the deployment catheter 300 of the percutaneous access sheath assembly 150. The entire assembly 150 may travel over the guide wire 400 until its distal tapered portion is positioned just within the renal pelvis. As mentioned above, the distal tip 314 is preferably provided with a pair of radiopaque tip markers 316a, 316b to aid placement. The jacket 200, which is on the exterior of the percutaneous access sheath assembly 150, facilitates the insertion because of its smooth, low profile exterior.

Following the insertion of the percutaneous access sheath assembly 150, the access sheath 100 may be expanded and released from the jacket 200. This may be accomplished by inflating, at least partially, the balloon 310 (not visible in FIG. 10) and radially expanding the access sheath 100 until the jacket 200 separates, preferably along the longitudinal axis of the jacket 200. As discussed above, the balloon 310 is arranged within the distal section 110 of the percutaneous access sheath 100, which is itself arranged within the restraint section 210 of the jacket 200. Thus, inflating the balloon 310 causes the distal section 110 of the percutaneous access sheath 100 to expand, tearing or separating the restraint section 210 of the jacket 200 preferably along its longitudinal axis.

After the sheath 100 is released from the jacket 200, the balloon 310 may be fully inflated to expand the distal section 110 of the percutaneous access sheath to its full cross-sectional profile. See FIG. 11. In one embodiment, the balloon 310 is inflated by providing a pump (e.g., a high pressure balloon inflation syringe) with about 20-25 cc of a diluted contrast media (e.g., a 50% solution of Renografin® and sterile saline). After removing the air from the pump and associated tubing, the pump may be attached to the inflation/deflation port of the central balloon shaft. Preferably, under fluoroscopic control, the dilute contrast media is slowly injected until a maximum pressure of about 12 bar is achieved. Inflation pressure is preferably maintained for a minimum of about 60 seconds to reduce or eliminate any "waist" (i.e., partially unexpanded sections) that may remain along the length of the expanded sheath 100.

In some embodiments, after the sheath 100 has been released from the jacket 200, the jacket 200 may be removed from the access sheath 100 and the surgical cite. In other embodiments, the jacket 200 may remain attached to the access sheath 100 during use. As explained above, in such embodiments, the jacket 200 may be securely attached to the access sheath by, for example, an adhesive or heat bond.

After the balloon 310 is inflated, it may be deflated to ease the removal of the deployment catheter 300. As discussed above, the inflation and deflation of the balloon 310 may be done via a pump connected to the port 320 of the deployment catheter 300, and preferably with a dilute contrast media being pumped, to better convey the state of the balloon.

Thus, the percutaneous access sheath 100 extends into the renal pelvis and provides a working lumen. See FIG. 12. The establishment of this working lumen may provide access for several procedures such as biopsy, stone extraction, antegrade endopyelotomy, and resection of transitional cell carcinoma of the upper urinary tract. As explained above, in the embodiments with a beveled edge 111, the leading edge 105a maintains positional purchase within the target tissue or organ while the trailing edge 105b provides the sheath 100 with an aperture to facilitate instrument maneuvering and visualization within the internal structure of the tissue or organ under examination or repair.

It will be apparent from the disclosure herein that the percutaneous access sheath 100, the percutaneous access sheath assembly 150, and/or the methods described herein may also find utility in a wide variety of diagnostic or therapeutic procedures that require an artificially created access tract. For example, the embodiments described herein may be used in many urological applications (e.g., the removal of ureteral strictures and stones, the delivery of drugs, RF devices and radiation for cancer treatment, etc.). In such applications, the percutaneous access sheath 100 may have a length of about 30-300 cm with an unexpanded diameter of about 7-20 French and an expanded diameter of about 14-60 French. The sheath 100 may also be used in many gastrointestinal applications, which require the introduction of a surgical retractor (e.g., to the removal gallstones and appendix procedures). In such applications, the percutaneous access sheath 100 may have a length of about 10-50 cm with an unexpanded diameter of about 3-15 French and an expanded diameter of about 15-60 French. The percutaneous access sheath 100 may also be used as an access catheter for many gastrointestinal applications (e.g., colon therapies, esophageal treatment and the treatment of bowel obstructions). In such applications, the percutaneous access sheath 100 may have a length of about 30-300 cm with an unexpanded diameter of about 7-40 French and an expanded diameter of about 14-120 French.

The sheath may also be used in many cardiovascular applications (e.g., to provide access for minimally invasive heart bypass, valve replacement or the delivery of drugs or angiogenesis agents). In such applications, the percutaneous access sheath 100 may have a length of about 30-300 cm with an unexpanded diameter of about 3-12 French and an expanded diameter of about 5-30 French. For vascular applications (e.g., minimally invasive access to the aorta or contralateral leg arteries for the treatment of, for example, an abdominal aortic aneurysm), the percutaneous access sheath 100 may have a length of about 30-300 cm with an unexpanded diameter of about 5-30 French and an expanded diameter of about 15-75 French. For gynecological applications (e.g., endometrial therapies, delivery of drugs, delivery of cancer agents, sterilization procedures, etc.), the percutaneous access sheath 100 may have a length of about 10-100 cm with an unexpanded diameter of about 3-20 French and an expanded diameter of about 6-60 French.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A percutaneous access sheath assembly for providing minimally invasive access for percutaneous nephrostomy or bladder access comprising:
    a balloon catheter having a balloon positioned on its distal end and which carries at least a first marker and a second marker;
    a circumferentially continuous elongate tubular structure having an unfoldable and expandable distal region including a distal end that forms a distal face which is beveled with respect to a longitudinal axis of the elongate tubular structure, a proximal region, and a tapered region between the distal region and the proximal region, the distal region is configured to unfold and expand from a first, folded, smaller cross-sectional profile to a second, greater cross-sectional profile radially around a longitudinal axis of the elongate tubular structure by the balloon that is positioned within an interior lumen of the distal region and removable so as to allow access by devices within a patient, wherein the balloon catheter is arranged such that the first marker is aligned with a front edge of the distal face in an expanded position and the second marker is aligned with a rear edge of the distal face in an expanded position, and
    a constraining releasable jacket sharing the same longitudinal axis as the elongate tubular structure and being carried by the percutaneous access sheath assembly to restrain at least a portion of said elongate tubular structure in said first, smaller cross-sectional profile; the constraining releasable jacket being releasable by tearing the constraining releasable jacket along a perforation.

2. The percutaneous access sheath assembly of claim 1, wherein the balloon is capable of being expanded in a radial direction to radially expand said portion of said elongate tubular structure.

3. The percutaneous access sheath assembly of claim 1, wherein when said elongate tubular structure is in said first, smaller cross-sectional profile it has an outer diameter of about 10 French to about 30 French.

4. The percutaneous access sheath assembly of claim 3, wherein when said elongate tubular structure is in said second, greater cross-sectional profile it has an outer diameter of about 15 to about 40 French.

5. The percutaneous access sheath assembly of claim 1, wherein when said elongate tubular structure is in said second, greater cross-sectional profile it has an inner diameter of about 12 to about 37 French.

6. The percutaneous access sheath assembly of claim 1, wherein the distal face forms an angle of about 45 to about 75 degrees with respect to the longitudinal axis of the elongate tubular structure.

7. The percutaneous access sheath assembly of claim 1, wherein the balloon catheter is positioned within the elongate tubular structure, the balloon catheter carrying said balloon to expand said portion of said elongate tubular structure from said first, smaller cross-sectional profile to said second, greater cross-sectional profile.

8. The percutaneous access sheath assembly of claim 1, wherein the constraining releasable jacket is attached to the elongate tubular structure.

9. The percutaneous access sheath assembly of claim 8, wherein the constraining releasable jacket comprises a perforation.

10. The percutaneous access sheath assembly of claim 8, wherein the constraining releasable jacket comprises a score line.

11. The percutaneous access sheath assembly of claim 8, wherein the constraining releasable jacket is formed of a material that will separate along a longitudinal axis as the elongate tubular structure is expanded in a radial direction.

12. The percutaneous access sheath assembly of claim 1, wherein the constraining releasable jacket comprises a perforation.

13. The percutaneous access sheath assembly of claim 1, wherein the constraining releasable jacket comprises a score line.

14. The percutaneous access sheath assembly of claim 1, wherein the constraining releasable jacket is formed of a material that will separate along a longitudinal axis as the elongate tubular structure is expanded in a radial direction.

15. The percutaneous access sheath assembly of claim 1, wherein the constraining releasable jacket is not attached to the elongate tubular structure.

16. The percutaneous access sheath assembly of claim 1, wherein when said portion of said elongate tubular structure is in said first smaller cross-sectional profile it is folded into at least 2 sections.

17. The percutaneous access sheath assembly of claim 1, wherein when said portion of said elongate tubular structure is in said first smaller cross-sectional profile it is folded into 2 to 6 sections.

18. The percutaneous access sheath assembly of claim 1, wherein said portion of said elongate tubular structure is capable of being expanded in response to a radial force.

19. The percutaneous access sheath assembly of claim 1, wherein the entire elongate tubular structure is restrained by the constraining releasable jacket in said first, smaller cross-sectional profile.

\* \* \* \* \*